(12) United States Patent
Stahurski

(10) Patent No.: US 6,551,318 B1
(45) Date of Patent: Apr. 22, 2003

(54) SPINAL COLUMN RETAINING APPARATUS

(75) Inventor: Terrance Stahurski, Seven Hills, OH (US)

(73) Assignee: Stahurski Consulting Inc., Seven Hills, OH (US)

( * ) Notice: Subject to any disclaimer, the term of this patent is extended or adjusted under 35 U.S.C. 154(b) by 219 days.

(21) Appl. No.: 09/625,961

(22) Filed: Jul. 26, 2000

(51) Int. Cl.⁷ .............................................. A61B 17/56
(52) U.S. Cl. ........................................................ 606/61
(58) Field of Search ............................ 606/60, 61, 72, 606/73

(56) References Cited

U.S. PATENT DOCUMENTS

| | | | |
|---|---|---|---|
| 4,987,892 A | * 1/1991 | Krag et al. ................... 606/61 |
| 5,047,029 A | 9/1991 | Aebi et al. |
| 5,254,118 A | 10/1993 | Mirkovic |
| 5,344,422 A | 9/1994 | Frigg |
| 5,474,551 A | * 12/1995 | Finn et al. .................... 606/61 |
| 5,545,167 A | 8/1996 | Lin |
| 5,562,662 A | 10/1996 | Brumfield et al. |
| 5,611,800 A | * 3/1997 | Davis et al. ................... 606/61 |
| 5,643,262 A | * 7/1997 | Metz-Stavenhagen et al. ... 606/61 |
| 5,645,544 A | 7/1997 | Tai et al. |
| 5,662,651 A | 9/1997 | Tornier et al. |
| 5,667,506 A | * 9/1997 | Sutterlin ....................... 606/61 |
| 5,676,703 A | * 10/1997 | Gelbard ........................ 623/17 |
| 5,688,275 A | * 11/1997 | Koros et al. .................. 606/61 |
| 5,693,053 A | 12/1997 | Estes |
| 5,741,255 A | 4/1998 | Krag et al. |
| 5,810,816 A | 9/1998 | Roussouly et al. |
| 5,810,819 A | 9/1998 | Errico et al. |
| 5,876,403 A | * 3/1999 | Shitoto ......................... 606/61 |
| 5,885,285 A | 3/1999 | Simonson |
| 5,938,663 A | * 8/1999 | Petreto ......................... 606/61 |
| 5,976,135 A | 11/1999 | Sherman et al. |
| 6,015,409 A | 1/2000 | Jackson |
| 6,063,089 A | * 5/2000 | Errico et al. .................. 606/61 |
| 6,238,396 B1 | * 5/2001 | Lombardo .................... 606/61 |
| 6,283,967 B1 | * 9/2001 | Troxell et al. ................ 606/61 |

* cited by examiner

Primary Examiner—Ralph A. Lewis
(74) Attorney, Agent, or Firm—Tarolli, Sundheim, Covell & Tummino L.L.P.

(57) ABSTRACT

An apparatus (10) for use in retaining vertebrae (12) of a spinal column (14) in a desired spatial relationship. The apparatus (10) comprises a spinal rod (16) for extending along the spinal column (14) and a hook shaped coupling member (24). The spinal rod (16) is laterally insertable into the hook shaped coupling member (24). The apparatus (10) further comprises a part for attaching to at least one vertebra (12) and a connecting element (66) for extending laterally between the hook shaped coupling member (24) and the part. The connecting element (66) has a first end (70) for attaching to the hook shaped coupling member (24) and a second end (72) for attaching to the part. The hook shaped coupling member (24) is rotatable in a first plane relative to the first end (70) of the connecting element (66) to enable a change in an angular position of the spinal rod (16) relative to the connecting element (66). The connecting element (66) further is laterally adjustable between the hook shaped coupling member (24) and the part to enable a change of the lateral distance between the spinal rod (16) and the part.

7 Claims, 4 Drawing Sheets

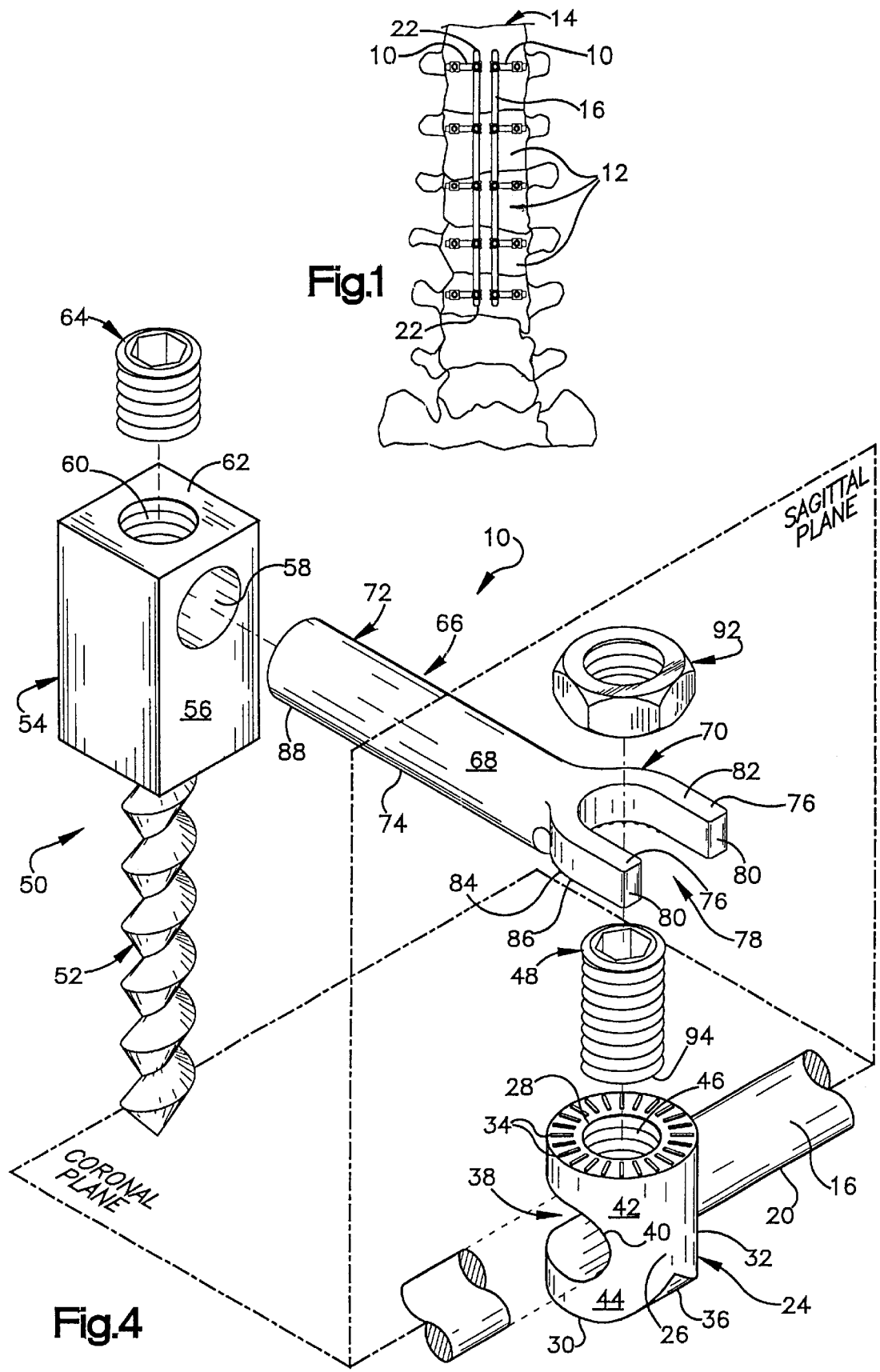

US 6,551,318 B1

SPINAL COLUMN RETAINING APPARATUS

TECHNICAL FIELD

The present invention relates to an apparatus that is used to retain vertebrae of a spinal column in a desired spatial relationship.

BACKGROUND OF THE INVENTION

A known apparatus for retaining vertebrae of a spinal column in a desired spatial relationship includes a spinal rod that extends along the spinal column and is fixed relative to at least one vertebra of the spinal column. Typically, a fastener is fixed to a vertebrae and a connector is fixed to the fastener and the spinal rod.

A need exists for an apparatus for retaining vertebrae of a spinal column in a desired spatial relationship and that allows changes in both the angular position of the spinal rod to the connector and the distance from the fastener to the spinal rod. The apparatus should also simplify the connection to a bent spinal rod.

SUMMARY OF THE INVENTION

The present invention is directed to an apparatus for use in retaining vertebrae of a spinal column in a desired spatial relationship. The apparatus comprises a spinal rod for extending along the spinal column and a hook shaped coupling member. The spinal rod is laterally insertable into the hook shaped coupling member. The apparatus further comprises a part for attaching to at least one vertebra and a connecting element for extending laterally between the hook shaped coupling member and the part. The connecting element has a first end for attaching to the hook shaped coupling member and a second end for attaching to the part. The hook shaped coupling member is rotatable in a first plane relative to the first end of the connecting element to enable a change in an angular position of the spinal rod relative to the connecting element. The connecting element further is laterally adjustable between the hook shaped coupling member and the part to enable a change of the lateral distance between the spinal rod and the part.

Another feature of the present invention is an apparatus that comprises a spinal rod for extending along the vertebrae and a coupling member having an opening for receiving the spinal rod. The coupling member has an external surface with a plurality of teeth. The apparatus further comprises a part for attaching to at least one vertebra and a connecting element for extending laterally between the coupling member and the part. The connecting element has a first end for attaching to the coupling member and a second end for attaching to the part. The first end of the connecting element has teeth for engaging the teeth of the coupling member. The coupling member is rotatable in a first plane relative to the first end of the connecting element to enable a change in an angular position of the spinal rod relative to the connecting element. The connecting element further is laterally adjustable between the coupling member and the part to enable a change of the lateral distance between the spinal rod and the part.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic view of a portion of a spinal column with two retaining apparatuses of the present invention maintaining a desired spatial relationship between vertebrae of the spinal column;

FIG. 3a is a view taken along line 3a—3a of FIG. 2a;

FIG. 4 is an exploded perspective view of the present invention;

DESCRIPTION OF THE PREFERRED EMBODIMENTS

Figure 2A:
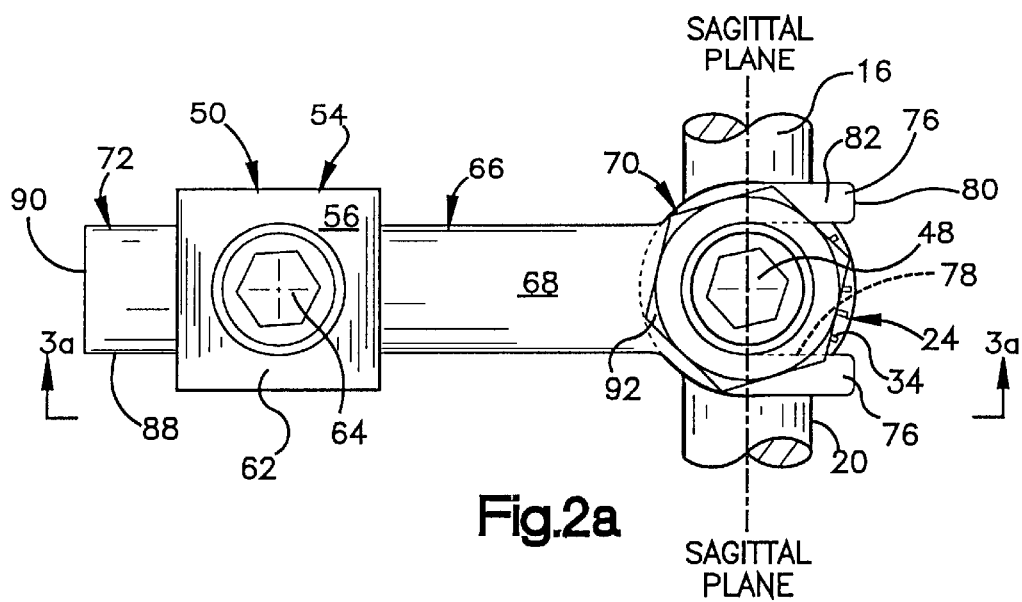
FIG. 2a is a top view of a retaining apparatus embodied FIG. 1.
Figure 2B:
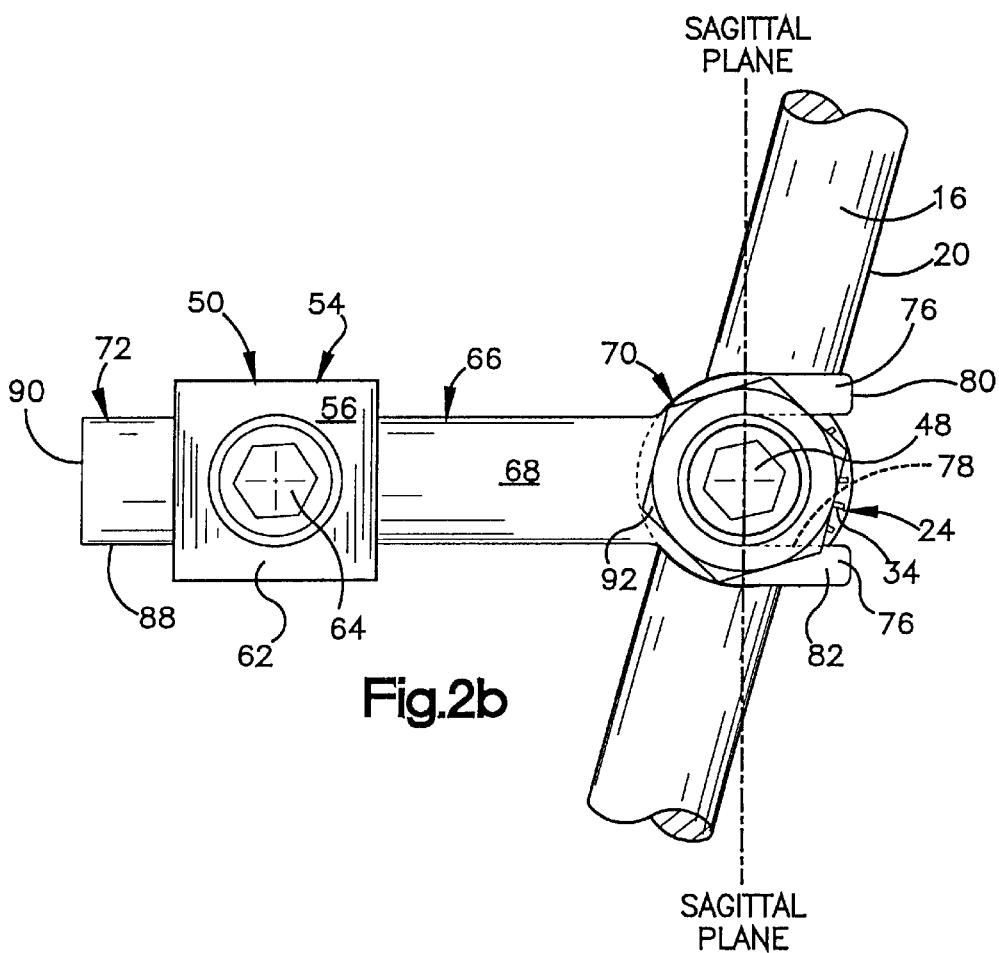
FIG. 2b is a view of the apparatus of FIG. 2a showing an adjustment in the coronal plane.

FIG. 1 shows a view of a portion of a spinal column 14 with two spinal column retaining apparatuses 10 maintaining a desired spatial relationship between vertebrae 12 of the spinal column 14. Each apparatus 10 includes a longitudinal member or spinal rod 16 for extending along a portion of the spinal column 14. The spinal rod 16 has a circular cross-section 18 (FIG. 3a) with a cylindrical outer surface 20 (FIGS. 2a, 2b, and 4). The spinal rod 16 has two end surfaces 22 that extend perpendicular to the cylindrical outer surface 20. The distance between the two end surfaces 22 defines the length of the spinal rod 16. The spinal rod 16 has a length that is sufficient to span at least two vertebrae 12. The spinal rod 16 in each apparatus 10 of FIG. 1 spans five vertebrae 12.

The spinal rod 16 may be bent, as desired, along its length to conform to a desired curvature of the spinal column 14. The spinal rod 16 may be bent in all or any of three possible anatomic planes. The three possible anatomic planes are the coronal plane, the sagittal plane, and the transverse plane. The spinal rod 16 is constructed from a single piece of stainless steel or another biocompatible material.

Figure 3A:
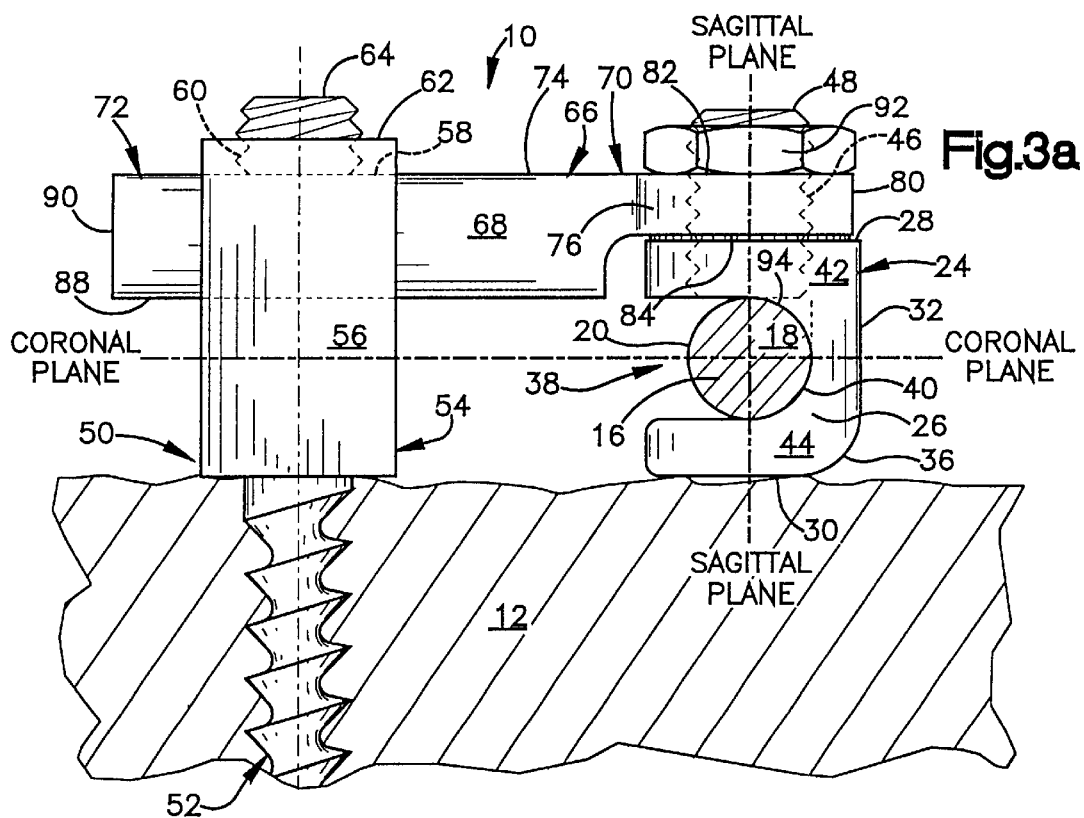

As best shown in FIG. 3a, the apparatus also includes a hook shaped coupling member 24 for receiving the spinal rod 16. Preferably, the hook shaped coupling member 24 has a cylindrical main body 26 (FIG. 4). The diameter of the cylindrical main body 26 is approximately twice the diameter of the spinal rod 16. The cylindrical main body 26 extends from an upper surface 28 to a lower surface 30. The distance from the upper surface 28 to the lower surface 30 is approximately equal to the diameter of the cylindrical main body 26 of the hook shaped coupling member 24.

As best shown in FIG. 4, the upper surface 28 extends perpendicular to an outer surface 32 of the cylindrical main body 26 of the hook shaped coupling member 24. The upper surface 28 is flat and includes a plurality of radially extending teeth 34. The lower surface 30 of the cylindrical main body 26 of the hook shaped coupling member 24 is curved. A majority of the lower surface 30 extends perpendicular to the outer surface 32 of the cylindrical main body 26 of the hook shaped coupling member 24; however, the lower surface 30 has an upward curve 36 near one edge.

An elongated slot 38 extends through the cylindrical main body 26 in a location approximately equidistant to the upper surface 28 and the lower surface 30 and on a side opposite to the upward curve 36 on the lower surface 30. The elongated slot 38 extends approximately three-quarters of the distance through the cylindrical main body 26 of the hook shaped coupling member 24. The elongated slot 38 extends radially inwardly through the cylindrical main body 26 of the hook shaped coupling member 24 until reaching a central axis. After reaching the central axis, the elongated slot 38 forms a semi-circular end 40. The elongated slot 38 has a width that is equal to or greater than the diameter of the cylindrical outer surface 20 of the spinal rod 16. The width of the elongated slot 38 illustrated in FIG. 3a is approximately equal to the diameter of the cylindrical outer surface 20 of the spinal rod 16. Thus, the spinal rod 16 may be laterally inserted into the elongated slot 38 in the hook shaped coupling member 24 and pressed firmly against the semi-circular end 40 of is the elongated slot 38.

The elongated slot 38 divides the hook shaped coupling member 24 into two portions, an upper portion 42 and a lower portion 44, as shown in FIG. 4. The upper portion 42 extends from the upper surface 28 of the hook shaped coupling member 24 to an axis dividing the elongated slot 38. The lower portion 44 extends from the lower surface 30 to the axis dividing the elongated slot 38. The interior surfaces of the upper and lower portions 42 and 44 of the hook shaped coupling member 24 define the elongated slot 38.

The upper portion 42 of the hook shaped coupling member 24 includes a threaded bore 46 (FIG. 4) for receiving a setscrew 48. As shown in FIG. 3a, the threaded bore 46 extends from the center of the upper surface 28 of the cylindrical main body 26 of the hook shaped coupling member 24 to the elongated slot 38.

The apparatus further includes a part for attaching to at least one vertebra 16. In FIGS. 1–4, the part is a fastener or pedicle screw 50. The pedicle screw 50 (FIGS. 3a, 3b, and 4) has a threaded portion 52 and a head portion 54. The threaded portion 52 engages a vertebra 12 (FIGS. 3a and 3b) to fixedly mount the pedicle screw 50 to the vertebra 16. The head portion 54 of the pedicle screw 50 includes an orthogonal main body 56 that is located axially above a threaded portion 52 of the pedicle screw 50. As shown in FIG. 4, the head portion 54 has both a laterally extending bore 58 and an axially extending bore 60. The laterally extending bore 58 extends completely through the main body 56 of the head portion 54 of the pedicle screw 50. The laterally extending bore 58 is sized for receiving an end of a connecting element 66. As shown in FIG. 3a, the axially extending bore 60 extends from a flat top surface 62 of the main body 56 of the head portion 54 of the pedicle screw 50 to the laterally extending bore 58 within the main body 56 of the head portion 54 of the pedicle screw 50. The axially extending bore 60 is threaded for receiving a setscrew 64.

The apparatus further includes a connecting element 66 for extending laterally between the hook shaped coupling member 24 and the screw 50. The connecting element 66 has a cylindrical main body portion 68 that extends between a first and a second end 70 and 72. The first end 70 is for attaching to the hook shaped coupling member 24 and the second end 72 is for attaching to the screw 50.

As shown in FIG. 4, the cylindrical main body portion 68 of the connecting element 66 has a laterally extending, cylindrical outer surface 74. The first end 70 of the connecting element 66 is bifurcated and has two branches 76. The two branches 76 extend from the main body portion 68 of the connecting element 66 and are separated by an elongated slot 78. Each branch 76 extends radially outward from the main body portion 68 of the connecting element 66 before extending laterally to the terminal end 80 of each branch 76.

The first end 70 of the connecting element 66 has an upper surface 82 and a lower surface 84 (FIG. 3a). The upper surface 82 is flat and extends from the cylindrical outer surface 74 of the main body portion 68. The lower surface 84 of the first end 70 is curved radially inwardly from the cylindrical outer surface 74 of the main body portion 68 of the connecting element 66. The inward distance of the curve of the lower surface 84 of the first end 70 is approximately equal to a length of the threaded bore 46 of the hook shaped coupling member 24. A plurality of teeth 86 is located on the lower surface 84 of the first end 70 for engaging the plurality of teeth 34 on the upper surface 28 of the hook shaped coupling member 24.

The second end 72 of the connecting element 66 has a cylindrical outer surface 88 that is identical to the main body portion 68 of the connecting element 66. A perpendicular surface forms a terminal end 90 of the second end 72 of the connecting element 66.

A first locking device secures the spinal rod 16 to the hook shaped coupling member 24 and also secures the hook shaped coupling member 24 to the first end 70 of the connecting element 66. Although multiple locking devices that secure each connection independently are contemplated by this invention, it is preferred that a single locking device be used to secure both connections.

The first locking device shown in FIGS. 2a–4 includes a setscrew 48 and a nut 92. The setscrew 48 threads into the threaded bore 46 that intersects the upper surface 28 of the hook shaped coupling member 24. After the spinal rod 16 is inserted into the hook shaped coupling member 24, the setscrew 48 may be tightened within the threaded bore 46 such that an end portion 94 (FIG. 3a) of the setscrew 48 contacts the cylindrical outer surface 20 of the spinal rod 16 to secure the spinal rod 16 within the elongated slot 38 of the hook shaped coupling member 24.

As shown in FIG. 3a, the setscrew 48 of the first locking device has a sufficient length such that when tightened into the threaded bore 46 of the hook shaped coupling member 24 to secure the spinal rod 16, a portion of the setscrew 48 extends outwardly of the upper surface 28 of the hook shaped coupling member 24. The first end 70 of the connecting element 66 is placed on the hook shaped coupling member 24 such that the flat upper surface 28 of the hook shaped coupling member 24 supports the lower surface 84 of the first end 70 of the connecting element 66 (FIG. 2a). In this position, the branches 76 of the first end 70 of the connecting element 66 extend around the outwardly extending portion of the setscrew 48 such that the setscrew 48 extends through the elongated slot 78 in the first end 70 and beyond the upper surface 82 of the first end 70 of the connecting element 66. The nut 92 of the first locking device is threaded onto the outwardly extending portion of the setscrew 48.

Prior to the nut 92 being tightened on the setscrew 48, the hook shaped coupling member 24 is rotatable relative to the connecting element 66. The rotation of the hook shaped coupling member 24 is rotation in a first plane and the axis of rotation extends through the center of the setscrew 48 of the first locking device. The rotation in the first plane enables a change in an angular position of the spinal rod 16 relative to the connecting member 66. Ideally, the first plane of rotation will be the coronal plane of the patient in which the invention is implanted. FIG. 2a illustrates the apparatus 10 of the present invention where the hook shaped coupling member 24 supports the spinal rod 16 such that the angle between the spinal rod 16 and the connecting element 66 is 90 degrees. FIG. 2b illustrates the apparatus 10 of the present invention where the hook shaped coupling member 24 has been rotated and the angle between the spinal rod 16 and the connecting element 66 is no longer 90 degrees. As illustrated in FIGS. 2a and 2b, the rotation of the hook shaped coupling member 24 causes the spinal rod 16 to move within the patient's coronal plane. When the nut 92 of the first locking device is tightened onto the setscrew 48, the hook shaped coupling member 24 becomes fixed relative to the connecting member 66 and will no longer rotate.

A second locking device secures the second end of the connecting element to the screw 50. In FIGS. 2a–4, the second locking device is a setscrew 64 for use in the axially extending threaded bore 60 of the head portion 54 of the pedicle screw 50. The second end 72 of the connecting element 66 is inserted into the laterally extending bore 58 in the main body 56 of the head portion 54 of the pedicle screw 50 such that the cylindrical outer surface 74 of the main body 68 of the connecting element 66 is supported within the laterally extending bore 58. As shown in FIG. 3a, the setscrew 64 is threaded into the axially extending threaded bore 60 until an end of the setscrew 64 contacts the cylindrical outer surface 74 of the connecting element 66 to fix the connecting element 66 relative the pedicle screw 50.

Figure 3B:
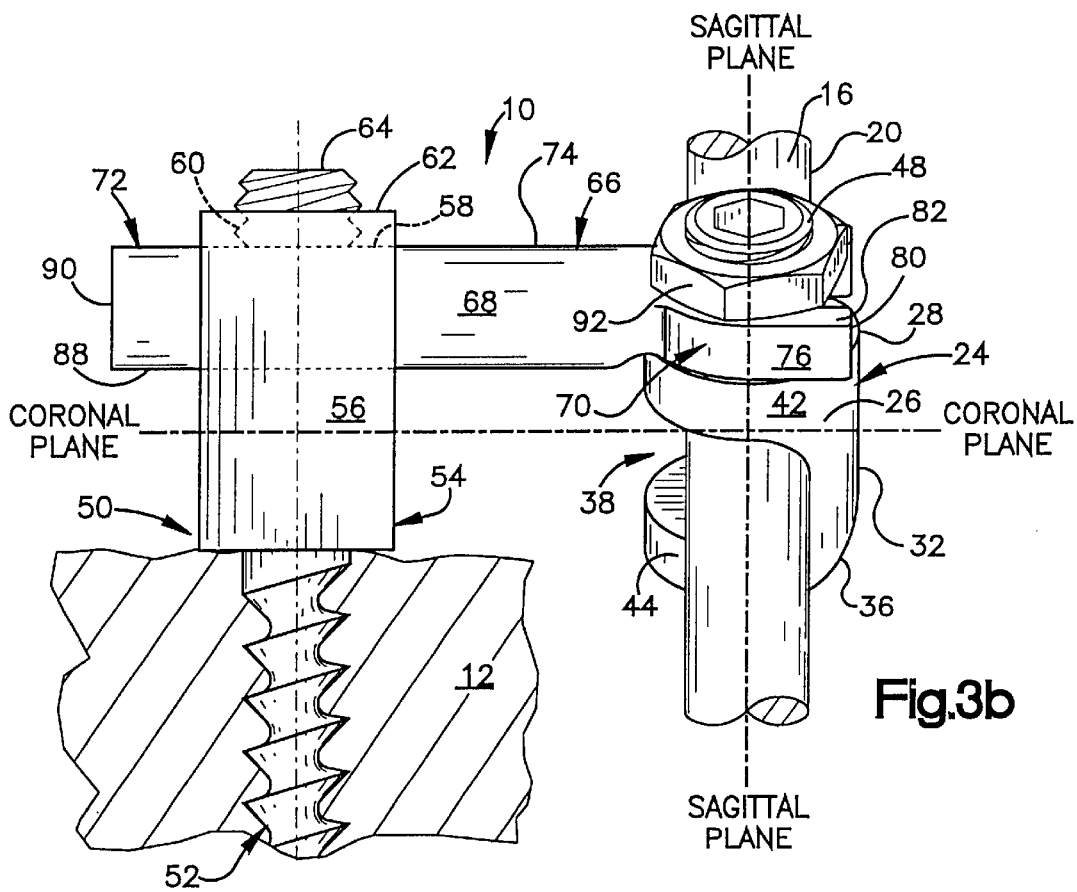
FIG. 3b is a view of the apparatus of FIG. 3a showing an adjustment in the sagittal plane.

Prior to the setscrew 64 fixing the second end 72 of the connecting element 66 to the pedicle screw 50, the connecting element 66 is both laterally adjustable within the laterally extending bore 58 of the head portion 54 of the pedicle screw 50 and rotatable within the laterally extending bore 58 of the head portion 54 of the pedicle screw 50. The connecting element 66 is laterally adjustable by moving the second end 72 of the connecting element 66 laterally within the laterally extending bore 58. The lateral adjustment enables a change in the lateral distance between the spinal rod 16 and the pedicle screw 50. The rotation of the connecting element 66 in the laterally extending bore 58 of the head portion 54 of the pedicle screw 50 is rotation in a second plane that is perpendicular to the first plane. The axis of rotation is a central axis of the connecting element 66. The rotation in the second plane enables a change in the angular position of the spinal rod 16 relative to the screw 50. Ideally, the second plane will be the sagittal plane of the patient. FIG. 3a illustrates the apparatus 10 of the present invention where the spinal rod 16 extends in a direction perpendicular to the pedicle screw 50. FIG. 3b illustrates the apparatus 10 of FIG. 3a after rotation of the connecting element 66 in the laterally extending bore 58 of the pedicle screw 50. As shown in FIG. 3b, the spinal rod 16 no longer extends in a direction perpendicular to the pedicle screw 50. As illustrated in FIGS. 3a and 3b, the rotation of the connecting element 66 in the laterally extending bore 58 of the head portion 54 of the pedicle screw 50 causes the spinal rod 16 to move within the sagittal plane.

Figure 5:
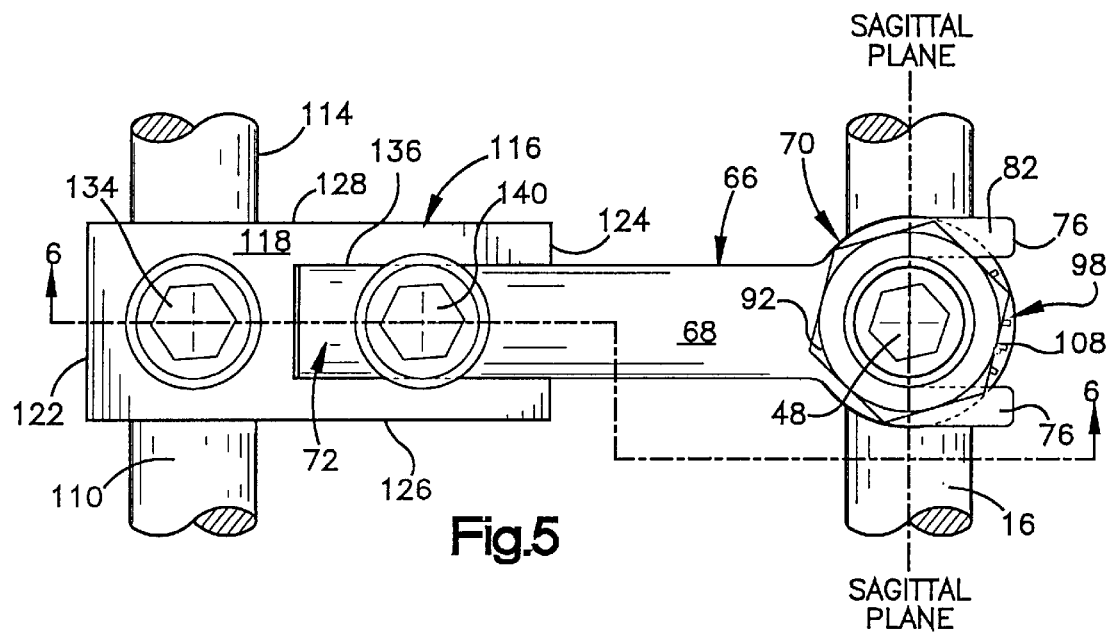
FIG. 5 is a top view of a second embodiment of the present invention.
Figure 6:
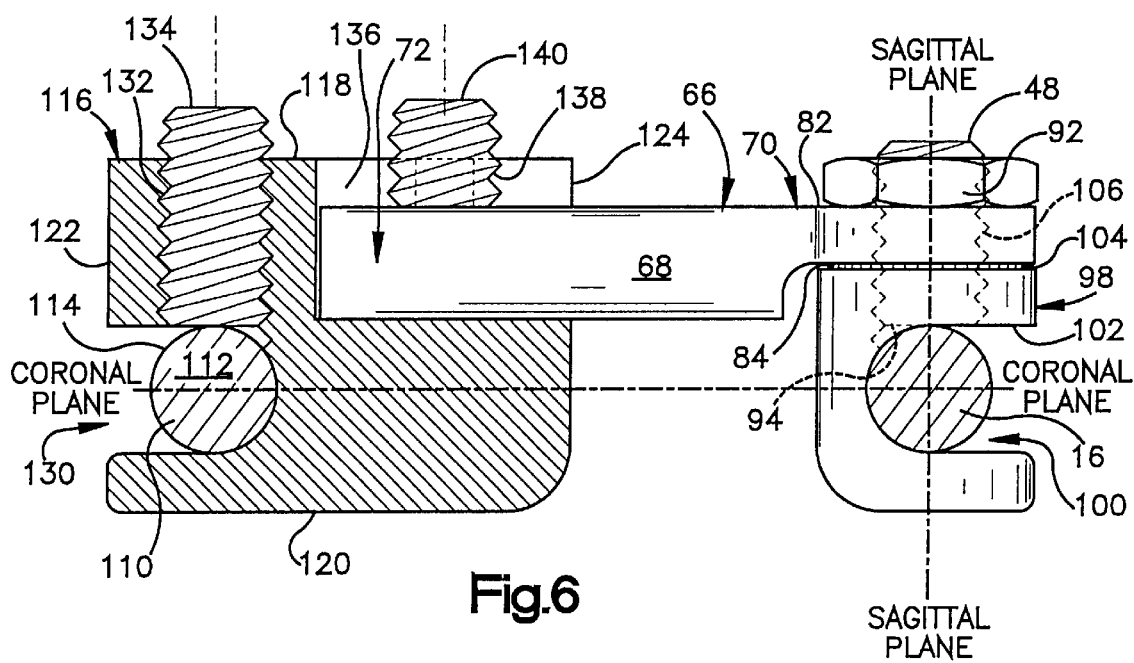
FIG. 6 is a view taken along line 6—6 of FIG. 5.

FIGS. 5 and 6 show a second embodiment of the present invention. In discussing the second embodiment, items that are similar in structure and function to those described with regard to the first embodiment will have similar numbers.

The apparatus 10 in FIGS. 5 and 6 is a rod-to-rod or transverse connector. The transverse connector interconnects rods that are connected to vertebrae and thus is used to retain vertebrae 12 of a spinal column 14 in a desired spatial relationship.

The transverse connector includes a first spinal rod 16. The first spinal rod 16 is identical to the spinal rod 16 discussed with regard to the first embodiment of the invention. The first spinal rod 16 may be bent along its length to conform to a desired curvature of the spinal column 14.

The transverse connector further is associated with a coupling member 98 for securing the first spinal rod 16. The coupling member 98 may be hook shaped, as shown in FIG. 6 or may be any other shape. The coupling member 98 has a bore 100 for receiving the first spinal rod 16. The bore 100 extends completely through the coupling member 98 and defines an interior surface 102 that at least partially engages the first spinal rod 16. The coupling member 98 includes an upper surface 104 for engaging the connecting element 66. A threaded bore 106 (FIG. 6) extends from the upper surface 104 to the first spinal rod 16 engaging bore 100. A plurality of teeth 108 (FIG. 5) for engaging the connecting element 66 is located on the upper surface 104 of the coupling member 98.

The part in the embodiment of FIGS. 5 and 6 is a second spinal rod 110. The second spinal rod 110 is attached to at least one vertebra 12 in a location not illustrated in FIGS. 5 and 6. The second spinal rod 110 has a circular cross-section 112 with a cylindrical outer surface 114. The second spinal rod 110 has two ends (not shown) that extend perpendicular to the cylindrical outer surface 114. The distance between the two ends defines the length of the second spinal rod 110. The second spinal rod 110 has a length that is sufficient to enable the rod to span at least two vertebrae 12.

Generally, the second spinal rod 110 extends longitudinally along the spinal column 14. Like the first spinal rod 16, the second spinal rod 110 may be bent, as desired, along its length to conform to a desired curvature of the spinal column 14 in all or any of three possible anatomic planes. The second spinal rod 110 is constructed from a single piece of stainless steel or another biocompatible material.

The transverse connector also includes a connecting element 66 for extending laterally between the coupling member 98 and the second spinal rod 110. The connecting element 66 of FIGS. 5 and 6 is of a construction similar to the connecting element 66 discussed with regard to FIGS. 1–4. The first end 70 of the connecting element 66 has a plurality of teeth (not shown) on its lower surface 84 for engaging the plurality of teeth 108 on the coupling member 98.

Since both the coupling member 98 and the connecting element 66 have teeth, the need for interconnecting washers between the coupling member 98 and the connecting element 66 is eliminated. By eliminating the interconnecting washers, the assembly of the coupling member 98 to the connecting element 66 is simplified.

A first locking device is used to both secure the first spinal rod 16 to the coupling member 98 and to secure the coupling member 98 to the connecting element 66. Multiple devices may be used to independently secure each connection; however, a single device securing both connections is preferred. The first locking device in FIGS. 5 and 6 is a setscrew 48 and a nut 92. The setscrew 48 and the nut 92 are identical to those described with reference to FIGS. 2a–4.

A second locking device is used to secure the second spinal rod 110 to the connecting element 66. As with the first locking device, multiple locking devices are contemplated by this invention, however a single locking device is preferred. The second locking device shown in FIGS. 5 and 6 is a retainer assembly 116. The retainer assembly 116 has the shape of a rectangular box. Surfaces of the retainer assembly 116 include an upper surface 118, a lower surface 120, an outer-side surface 122, an inner-side surface 124, a front surface 126, and a rear surface 128. The retainer assembly 116 has two sections, a section for attaching to the second spinal rod 110 and a section for attaching to the connecting member 66.

The section of the retainer assembly 116 for attaching to the second spinal rod 110 is located near the outer-side surface 122 of the retainer assembly 116. The section includes a bore 130 extending from the front surface 126 of the retainer assembly 116 to the rear surface 128 of the retainer assembly 116. The bore 130 extends parallel to the outer-side surface 122 and is for receiving the second spinal rod 110. The bore 130 may be open to the outer-side surface 122, as shown in FIG. 6, or may be enclosed on all sides. If the bore 130 is open to the outer-side surface 122, the second spinal rod 110 may be laterally insertable into the bore 130. If the bore 130 is enclosed on all sides, in order to connect the second spinal rod 110 to the retainer assembly 116, an end of the second spinal rod 110 must be inserted into an opening of the bore 130 located on either the front surface 126 or the rear surface 128 of the retainer assembly 116. A bore 130 open on the outer-side surface 122, as illustrated in FIG. 6, is preferred.

A first threaded bore 132 extends through the retainer assembly 116 to intersect with the bore 130 receiving the second spinal rod 110. A setscrew 134 is threaded into the first threaded bore 132 to fix the retainer assembly 116 to the second spinal rod 110.

The section of the retainer assembly 116 for attaching to the connecting element 66 is located near an upper surface 118 of the retainer assembly 116. The section has a laterally extending channel 136 that extends into the retainer assembly 116 from the inner-side surface 124. As illustrated in FIG. 6, the channel 136 is open to the upper surface 118 of the retainer assembly 116. The channel 136 has a width sufficient to receive the second end 72 of the connecting element 66 and a depth sufficient to retain the second end 72 of the connecting element 66, when received, below the upper surface 118 of the retainer assembly 116. A second threaded bore 138 extends into the channel 136 from the upper surface 118 of the retainer assembly 116. The second threaded bore 138 is located near the inner-side surface 124 of the retainer assembly 116 and receives a setscrew 140 for fixing the connecting element 66 relative to the retainer assembly 116.

Like the embodiment of the invention illustrated in FIGS. 1–4, the transverse connector illustrated in FIGS. 5 and 6 allows lateral adjustment of the distance between the second spinal rod 110 and the coupling member 98, as well as rotation of the rods in two planes, the coronal plane and the sagittal plane. Since the length of the channel 136 in the retainer assembly 116 may limit the amount of lateral adjustment, the second end 72 of the connecting element 66 may be cut to allow for additional lateral adjustment. The second end of the connecting element 66 is laterally movable within the channel 136 of the retainer assembly 116 for adjusting the lateral distance between the second spinal rod 110 and the coupling member 98. The second end 72 of the connecting element 66 may be rotated within the channel 136 of the retainer assembly 116 to enable a change in the angular position of the first spinal rod 16 relative to the second spinal rod 110. By tightening the setscrew 140 in the threaded bore 138 extending into the channel 136 of the retainer assembly 116, the connecting element 66 becomes fixed relative the second spinal rod 110. Also, the coupling member 98 is rotatable relative to the first end 70 of the connecting element 66 for enabling an adjustment of the angular position between the connecting element 66 and the first spinal rod 16. By tightening the nut 92 of the first locking device onto the setscrew 48 of the first locking device, the coupling member 98 becomes fixed relative to the connecting element 66.

From the above description of the invention, those skilled in the art will perceive improvements, changes and modifications. Examples of such improvements, changes, and modifications include changes to the location and design of the plurality of teeth on the coupling member 108 and the connecting element 66 and the structure of the first and second locking devices. Such improvements, changes and modifications within the skill of the art are intended to be covered by the appended claims.

Having described the invention, the following is claimed:

1. An apparatus for use in retaining vertebrae of a spinal column in a desired spatial relationship comprising:

a spinal rod for extending along the spinal column;

a hook shaped coupling member, the spinal rod being laterally insertable into the hook shaped coupling member;

a part for attaching to at least one vertebra;

a connecting element for extending laterally between the hook shaped coupling member and the part, the connecting element having a first end for attaching to the hook shaped coupling member and a second end for attaching to the part;

the hook shaped coupling member being rotatable in a first plane relative to the first end of the connecting element to enable a change in an angular position of the spinal rod relative to the connecting element;

the connecting element further being laterally adjustable between the hook shaped coupling member and the part to enable a change of the lateral distance between the spinal rod and the part;

the connecting element being rotatable relative to the part to enable a change in an angular position of the spinal rod relative to the part, rotation of the connecting element being in a second plane that is perpendicular to the first plane; and a first locking device for securing the spinal rod to the hook shaped coupling member and the hook shaped coupling member to the connecting element, the first locking device being a setscrew and a nut;

a threaded bore extending from an upper surface of the hook shaped coupling member to an interior surface receiving the spinal rod, the setscrew of the first locking device being received by the threaded bore and when tightened securing the spinal rod to the hook shaped coupling member, when securing the spinal rod to the hook shaped coupling member the setscrew of the first locking device extends outwardly of the upper surface of the hook shaped coupling member, the first end of the connecting element having a portion for receiving the outwardly extending setscrew, the nut being threaded onto the setscrew to attach the connecting element to the hook shaped coupling member, upon tightening the nut on the setscrew the hook shaped coupling member becoming fixed relative to the connecting element.

2. The apparatus of claim 1 further being defined by:

the connecting element having a plurality of teeth; and an upper surface of the hook shaped coupling member having a plurality of teeth for engaging the plurality of teeth of the connecting element.

3. An apparatus for use in retaining vertebrae of a spinal column in a desired spatial relationship comprising:

a spinal rod for extending along the spinal column;

a hook shaped coupling member, the spinal rod being laterally insertable into the hook shaped coupling member;

a part for attaching to at least one vertebra;

a connecting element for extending laterally between the hook shaped coupling member and the part, the connecting element having a first end for attaching to the hook shaped coupling member and a second end for attaching to the part;

the hook shaped coupling member being rotatable in a first plane relative to the first end of the connecting element to enable a change in an angular position of the spinal rod relative to the connecting element;

the connecting element further being laterally adjustable between the hook shaped coupling member and the part to enable a change of the lateral distance between the spinal rod and the part;

the connecting element being rotatable relative to the part to enable a change in an angular position of the spinal rod relative to the part, rotation of the connecting element being in a second plane that is perpendicular to the first plane;

a first locking device for securing the spinal rod to the hook shaped coupling member and the hook shaped coupling member to the connecting element; and a second locking device for securing the part to the connecting element;

the part for attaching to at least one vertebra being a fastener, the fastener having a head portion located axially above a threaded portion, the head portion having a laterally extending bore and an axially extending bore, the laterally extending bore extending completely through the head portion of the fastener, the axially extending bore being threaded and extending from a top surface of the head portion of the fastener to the laterally extending bore, the second locking device being a setscrew which threads into the threaded bore to secure the connecting element relative to the fastener.

4. An apparatus for use in retaining vertebrae of a spinal column in a desired spatial relationship comprising:

a spinal rod for extending along the vertebrae;

a coupling member having an opening for receiving the spinal rod, the coupling member having an upper surface with a plurality of teeth;

a part for attaching to at least one vertebra;

a connecting element for extending laterally between the coupling member and the part, the connecting element having a first end for attaching to the coupling member and a second end for attaching to the part, the first end of the connecting element having teeth for engaging the teeth of the coupling member;

the coupling member being rotatable in a first plane relative to the first end of the connecting element to enable a change in an angular position of the spinal rod relative to the connecting element;

the connecting element further being laterally adjustable between the coupling member and the part to enable a change of the lateral distance between the spinal rod and the part;

the connecting element being rotatable relative to the part to enable a change in angular-position of the spinal rod relative to the part, rotation of the connecting element being in a second plane that is perpendicular to the first plane; and a first locking device for securing the spinal rod to the coupling member and the coupling member to the connecting element, the first locking device being a setscrew and a nut;

a threaded bore extending from the upper surface of the coupling member to an interior surface receiving the spinal rod, the setscrew of the first locking device being received by the threaded bore and when tightened securing the spinal rod to the coupling member, when securing the spinal rod the setscrew of the first locking device extends outwardly of the upper surface of the coupling member, the first end of the connecting element having a portion for receiving the outwardly extending setscrew, the nut being threaded onto the setscrew to attach the connecting element to the coupling member, upon tightening the nut on the outwardly extending setscrew the coupling member becoming fixed relative to the connecting element.

5. An apparatus for use in retaining vertebrae of a spinal column in a desired spatial relationship comprising:

a spinal rod for extending along the vertebrae;

a coupling member having an opening for receiving the spinal rod, the coupling member having an upper surface with a plurality of teeth;

a part for attaching to at least one vertebra;

a connecting element for extending laterally between the coupling member and the part, the connecting element having a first end for attaching to the coupling member and a second end for attaching to the part, the first end of the connecting element having teeth for engaging the teeth of the coupling member;

the coupling member being rotatable in a first plane relative to the first end of the connecting element to enable a change in an angular position of the spinal rod relative to the connecting element;

the connecting element further being laterally adjustable between the coupling member and the part to enable a change of the lateral distance between the spinal rod and the part;

the connecting element being rotatable relative to the part to enable a change in angular position of the spinal rod relative to the part, rotation of the connecting element being in a second plane that is perpendicular to the first plane;

a first locking device for securing the spinal rod to the coupling member and the coupling member to the connecting element; and a second locking device for securing the part to the connecting element;

the part for attaching to at least one vertebra being a fastener.

6. The apparatus as in claim 5 further being defined by:

the fastener having a head portion located axially above a threaded portion, the head portion having a laterally extending bore and an axially extending bore, the laterally extending bore extending completely through the head portion of the fastener, the axially extending bore being threaded and extending from a top surface of the head portion of the fastener to the laterally extending bore, the second locking device being a setscrew which threads into the threaded bore to secure the connecting element relative to the fastener.

7. An apparatus for use in retaining vertebrae of a spinal column in a desired spatial relationship comprising:

a spinal rod for extending along the vertebrae;

a coupling member having an opening for receiving the spinal rod, the coupling member having an upper surface with a plurality of teeth;

a part for attaching to at least one vertebra;

a connecting element for extending laterally between the coupling member and the part, the connecting element having a first end for attaching to the coupling member and a second end for attaching to the part, the first end of the connecting element having teeth for engaging the teeth of the coupling member;

the coupling member being rotatable in a first plane relative to the first end of the connecting element to enable a change in an angular position of the spinal rod relative to the connecting element;

the connecting element further being laterally adjustable between the coupling member and the part to enable a change of the lateral distance between the spinal rod and the part;

the connecting element being rotatable relative to the part to enable a change in angular position of the spinal rod relative to the part, rotation of the connecting element being in a second plane that is perpendicular to the first plane;

a first locking device for securing the spinal rod to the coupling member and the coupling member to the connecting element; and a second locking device for securing the part to the connecting element;

the part for attaching to at least one vertebra being a second spinal rod, the second locking device being a retainer assembly for securing the second spinal rod to the connecting element, the retainer assembly having a bore for receiving the second spinal rod, a first threaded bore intersecting the bore, the first threaded bore having a setscrew for securing the second spinal rod relative to the retainer assembly, the retainer assembly further having a laterally extending channel for receiving the second end of the connecting element, a second threaded bore intersecting the channel, a setscrew securing the connecting element relative to the retainer assembly.

* * * * *